United States Patent [19]
de Roulhac et al.

[11] Patent Number: 5,752,928
[45] Date of Patent: May 19, 1998

[54] GLAUCOMA PRESSURE REGULATOR

[75] Inventors: Joseph Gregoire de Roulhac; John Luke Ruiz, both of Santa Barbara; C. Eric Olsen, Carpinteria, all of Calif.

[73] Assignee: RDO Medical, Inc., Carpinteria, Calif.

[21] Appl. No.: 891,966

[22] Filed: Jul. 14, 1997

[51] Int. Cl.$^6$ .................................................. A61M 5/00
[52] U.S. Cl. .................................................. 604/8; 604/9
[58] Field of Search .................... 604/8, 9, 10, 294, 604/289; 623/4

[56] References Cited

U.S. PATENT DOCUMENTS

| | | | |
|---|---|---|---|
| Re. 35,390 | 12/1996 | Smith | 604/8 |
| 479,407 | 7/1892 | Drennan | 604/9 X |
| 3,853,126 | 12/1974 | Schulte | 604/8 |
| 4,037,604 | 7/1977 | Newkirk | 128/350 |
| 4,479,796 | 10/1984 | Kallok | 604/8 X |
| 4,554,918 | 11/1985 | White | 604/10 |
| 4,604,087 | 8/1986 | Joseph | 604/9 |
| 4,729,761 | 3/1988 | White | 604/8 |
| 4,750,901 | 6/1988 | Molteno | 604/8 |
| 4,787,885 | 11/1988 | Binder | 604/8 |
| 4,886,488 | 12/1989 | White | 604/9 |
| 4,964,850 | 10/1990 | Bouton | 604/8 X |
| 5,073,163 | 12/1991 | Lippman | 604/9 |
| 5,137,523 | 8/1992 | Peerless et al. | 604/8 X |
| 5,222,982 | 6/1993 | Ommaya | 604/8 X |
| 5,338,291 | 8/1994 | Speckman et al. | 604/8 X |
| 5,370,607 | 12/1994 | Memmen | 604/9 X |
| 5,378,228 | 1/1995 | Schmalzried et al. | 604/8 |
| 5,476,460 | 12/1995 | Montalvo | 604/8 X |
| 5,558,630 | 9/1996 | Fisher | 604/8 |

*Primary Examiner*—Sam Rimell
*Attorney, Agent, or Firm*—Jack C. Munro

[57] ABSTRACT

The subject invention is an implant for relieving abnormally high intraocular pressures with the anterior chamber of an eyeball which is associated with the disease called glaucoma. The implant includes a base plate which is formed of a thin, flexible, preferably rubber material such as silicone rubber. Mounted on the base plate is a housing with the housing including an internal chamber. The housing has an open front end covered by a canopy which is mounted on the base plate. The rear end of the housing is attached to a tube. Aqueous humor is to be conducted through the tube, through the porous block and then through the access opening into the ambient. The housing is mounted within a mounting pocket formed within the base plate.

7 Claims, 2 Drawing Sheets

GLAUCOMA PRESSURE REGULATOR

BACKGROUND OF THE INVENTION

1) Field of the Invention

This invention relates to an ophthalmological device which is designed to be incorporated with the eyeball of a human for the relief of high intraocular pressures of the anterior chamber of the eyeball characteristic of the disease of glaucoma.

2) Description of the Prior Art

A common disease of the eye is glaucoma. Within the anterior chamber of the eyeball is located a liquid called the aqueous humor. This liquid is normally under a certain pressure with this pressure being in the range of ten to twenty millimeters of mercury. In the disease of glaucoma, this pressure increases uncontrollably and if the pressure gets too severe, the individual can go blind.

In the past, there have been different techniques to relieve this excessive pressure and a significant amount of money is spent each year on drops that are to be placed on the eye that can be minimally effective. Additionally, there are numerous surgical techniques in order to relieve this pressure. One of the most common surgical techniques is to cut an opening in the anterior chamber of the eyeball which provides an outlet for some of the liquid contained in the eyeball thereby relieving the the pressure. This opening is then sutured. The disadvantage of this technique is that initially the pressure of the liquid in the anterior chamber is diminished below the desired level to atmospheric pressure. This lack of pressure within the eyeball can cause certain undesirable medical problems such as corneal dystrophy. As time goes on, normally the pressure will again rebuild to its original adverse level which will require duplicating of the surgical procedure or initiating some other procedure.

To overcome the disadvantage of this foregoing technique, there has been manufactured a valve assembly which is to be mounted in conjunction with the eyeball and located within the opening cut into the eyeball. It is the function of this valve to activate if a certain pressure level is exceeded and provide a drainage channel for some of the liquid contained within the anterior chamber of the eyeball thereby relieving the pressure. The disadvantage of this valve is that it frequently malfunctions thereby requiring replacement or removal of the valve unit.

Another known device to relieve intraocular pressure has to do with utilizing a balloon operating a pump and check valve as opposed to sole use of a check valve. This pump is to release liquid when pressure is applied to the balloon. This pressure to the balloon is to be applied by the natural blinking of the human eye or is to be applied by manual rubbing of one's eye. Again, this type of unit can be prone to malfunction.

There has been a need to construct an improved form of pressure relieving device to be mounted in conjunction with an eyeball which will continually relieve the pressure of the anterior chamber of the eyeball once the pressure has exceeded a predetermined level. This device should be substantially free of malfunction having no moving parts as necessitated by valves or pumps. Such a device has been defined within U.S. Pat. No. 5,073,163 issued Dec. 17, 1991 to a Myron E. Lippman which is owned by the assignee of record. However, this device has certain disadvantages. One of the disadvantages is that the eye, over a period of time, will create a sufficient amount of scar tissue that will eventually block the flow path of the liquid through the device. At that particular point in time, it would be necessary to replace the device. It would be desirable to design an intraocular pressure relief device that resists the blocking of the device by scar tissue within the eyeball.

The physical height of the Lippman prior art device should be decreased so as to minimize the capsule which will inherently be created on the eyeball when the device is installed. Another disadvantage of the Lippman device is that it requires a particular type of plastic block that included a mass of tiny through openings. Although this type of plastic block may be utilized, it is desirable to be able to utilize other types of fluid restrictors so as to not be limited to one specific type of fluid restrictor. A further disadvantage of the Lippman device is that it has sharp edges which pose problems with erosion of tissue and extrusion through the conjunctiva.

SUMMARY OF THE INVENTION

The device of the present invention utilizes a thin, flexible base plate which is to be constructed of a readily bendable material such as silicone rubber. This base plate includes a top surface and a bottom surface as well as a front edge and a bottom edge. Formed within the bottom surface of the base plate, and connecting with the bottom edge, is a mounting recess. The base plate also includes a pair of slots with a slot extending from each sidewall. The purpose of the slots is to enhance the flexibility of the base plate. The base plate is to be mounted within a flap of conjunctiva by a surgical procedure. Fixedly mounted within the mounting pocket is a housing with this housing having an internal chamber. One end of the internal chamber is connected with a tube and is to receive aqueous humor from the eyeball by means of the tube. The opposite end of the internal chamber is open but is covered by means of a canopy. It is the purpose of the canopy to substantially eliminate the growing of scar tissue on the eyeball in a manner that could obstruct a porous block of material mounted within the internal chamber of the housing. Aqueous humor is to be conducted through the tube and then through a porous block mounted in the internal chamber into the ambient exteriorly through the front end of the internal chamber.

The primary objective of the present invention is to construct a device which is designed to relieve the intraocular build-up of pressure within the anterior chamber of an eyeball which can be installed quickly and easily by a skilled surgeon.

Another objective of the present invention is to construct a device which prevents the intraocular build-up of pressure within the anterior chamber of the eyeball and which substantially eliminates the blocking of the flow path through the device over a period of time by the natural creation of scar tissue by the eyeball.

Another objective of the present invention is to construct a device that conforms easily to the globe shape of the eyeball. Another objective of the present invention is to construct a device that is to be mounted within the eyeball to aid in the forming of a fluid bleb.

DETAILED DESCRIPTION OF THE PREFERRED EMBODIMENT

Figure 1:
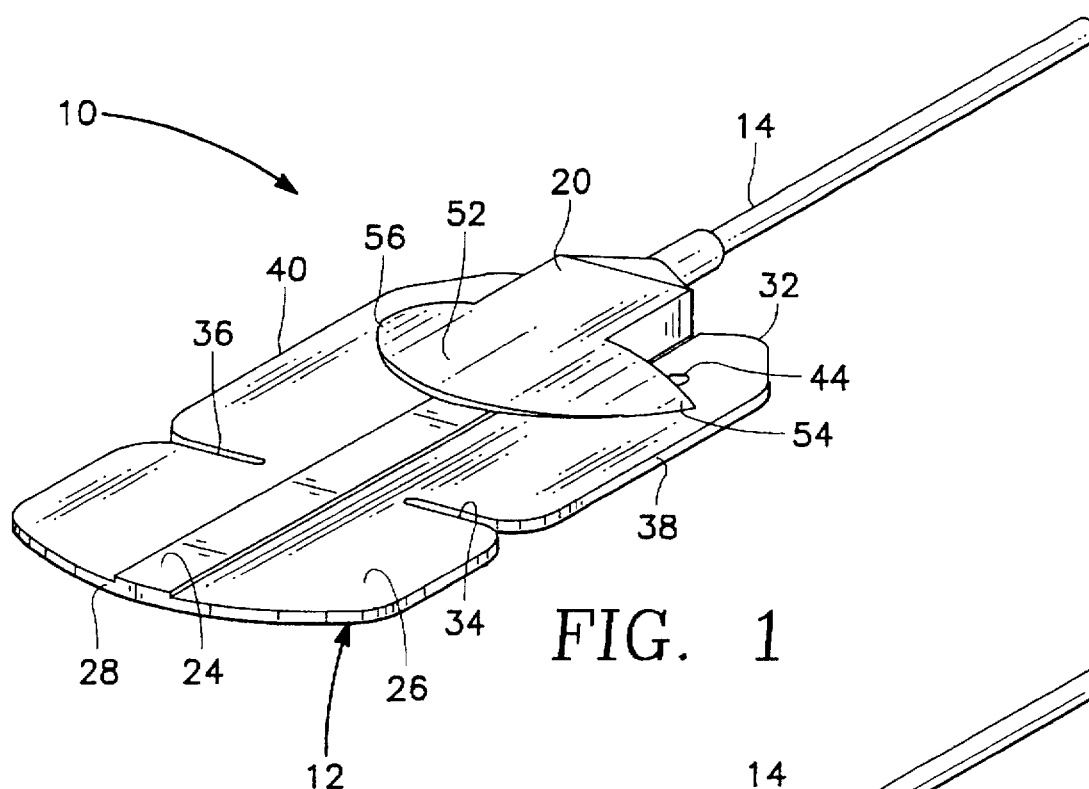
FIG. 1 is an isometric view of the glaucoma pressure regulator of the present invention with this isometric view being taken from the direction of the top surface of the regulator.
Figure 2:
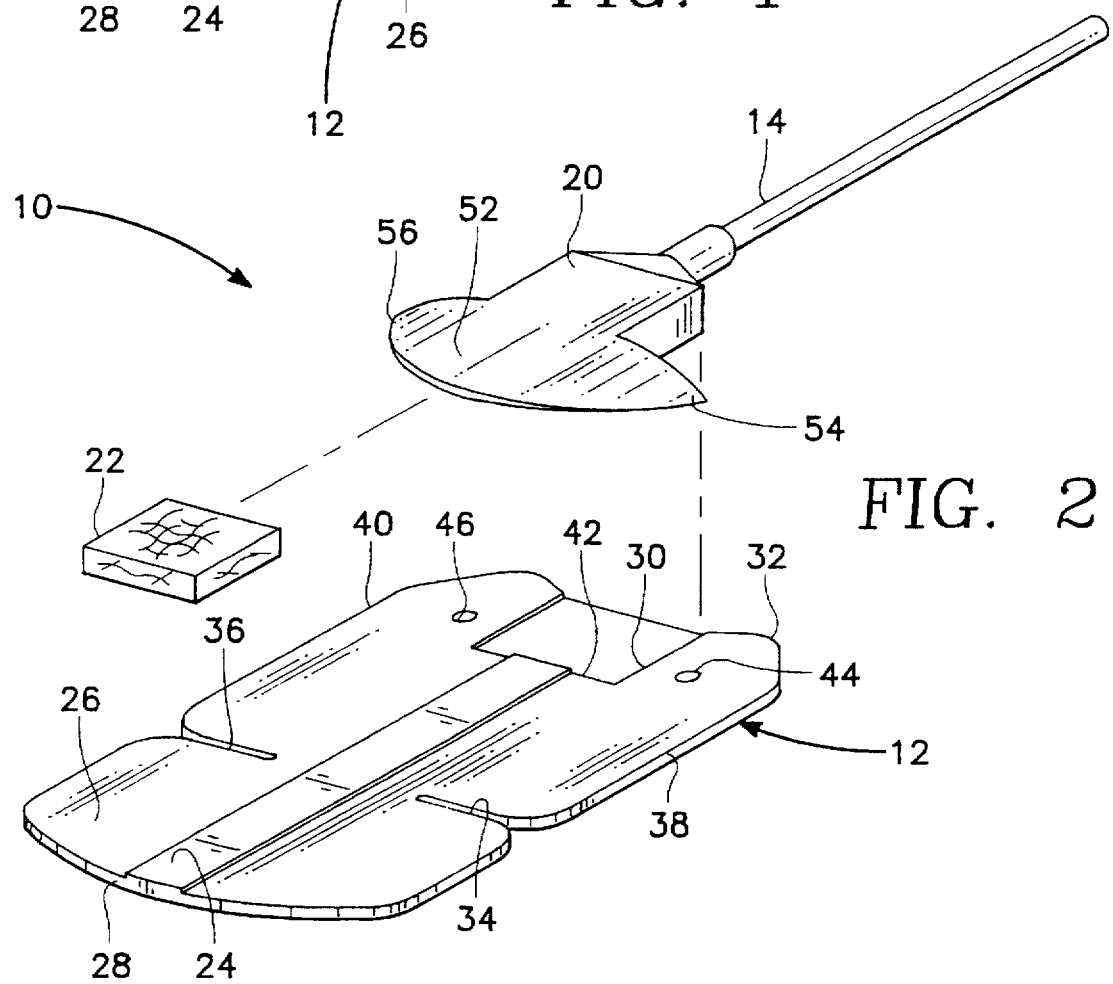
FIG. 2 is an isometric view of the glaucoma pressure regulator of the present invention similar to FIG. 1 but showing the different parts of the regulator in an exploded view.
Figure 3:
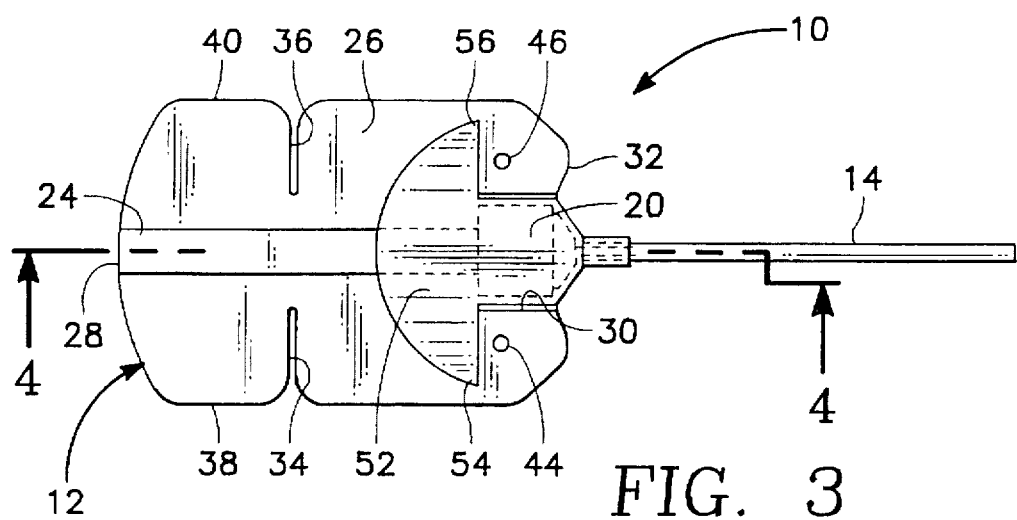
FIG. 3 is a top plan view of the glaucoma pressure regulator of the present invention.

Referring particularly to the drawings, there is shown the glaucoma pressure regulator 10 of this invention. The pressure regulator 10 includes a molded silicone rubber base plate 12. Although silicone rubber is currently the most desirable material of manufacture, it is considered to be within the scope of the invention that other exceedingly flexible materials could be utilized. It is important that the base plate 12 be very flexible so as to conform precisely to the globe of the eyeball when installed. A typical method of installation would be to make a surgical incision in the conjunctiva of the eyeball with this incision resulting in the creation of a flap which is to be folded outward exposing a concavity. Within this concavity is installed the base plate 12. The flap of the conjunctiva is then placed over the pressure regulator 10 and sutured closed. A twenty-one gauge needle is used to make an opening in the anterior chamber of the eyeball. The surgeon selects the desired length for the tube 14 to which it is then cut. The outer end of the tube 14 is then inserted through the opening produced by the twenty-one gauge needle with the end of the tube 14 extending into the anterior chamber. Subconjunctival antibiotics and steroids are then injected into the eyeball completing the surgical procedure.

The tube 14 will normally be constructed of a rubber material. The tube 14 includes a longitudinal internal through passage 16. The tube 14 is securely mounted within hole 15 of a housing 20. The aqueous humor from the anterior chamber of the eyeball is to be conducted through the passage 16 through hole 17 of housing 20, to within the confines of an internal chamber 18 formed in the housing 20. The housing 20 would normally be constructed of a plastic or rubber material. The internal chamber 18 is configured so as to receive in a close conforming manner a porous block 22. The porous block 22 can be constructed of plastic which includes a mass of tiny holes such as is defined within U.S. Pat. No. 5,073,163. Also, the block 22 can be constructed of a molded, open cell, high density, polymer with a nominal porosity of approximately eleven microns. This type of block is currently commercially available. Preferable material for the block 22 would have open cells or produces passageways for liquid. The liquid from the aqueous humor, which is under pressure from the anterior chamber, is slowly forced by this pressure slowly through the block 22. The restriction of the flow through the block 22 is for the purpose of maintaining a desired level of pressure within the anterior chamber with approximately fifteen millimeters of mercury or lower as preferred by the physician. However, the more porous the block 22, the lower the pressure. The less porous the block 22, the greater the pressure. Therefore, by selecting different porosities of the block 22, different levels of pressure within the anterior chamber can be achieved. This is desirable since, for different individuals, there can be a reasonably wide variance of pressure levels. Therefore, by selecting a particular porosity of the block 22, a pressure level variables can be achieved.

Typically, the thickness of the base plate 12 will be in the range of 0.3 millimeters. However, there is incorporated a strengthening rib 24 within the top surface 26 of the base plate 12. The height of this rib 24 is to be approximately 0.12 millimeters. It is the function of the rib 24 to supply a certain amount of rigidity along the longitudinal center axis of the base plate 12. The rib 24 extends from the front end 28 to a recess defined as a mounting pocket 30 which is formed within the base plate 12 directly adjacent the rear end 32. The mounting pocket 30 would normally be formed to a depth of approximately 0.12 millimeters.

It is to be noted that the front end 28 is curved. The reason for this is that it is desirable to eliminate the creation of any sharp edges. Sharp edges could be damaging to the eyeball. A preferable width of the base plate 12 would be about ten millimeters. The preferable length of the base plate 12 would be about fourteen millimeters. This device can have a larger or smaller plate 12 to accommodate differing needs such as in pediatric glaucoma where a smaller plate would be desirable.

In order to increase the flexibility of the base plate 12, it is desirable to include slots 34 and 36. Slot 34 extends from the left edge 38 of the base plate 12. Slot 36 extends from the right edge 40 of the base plate 12. Generally, the desired depth of each of the slots 34 and 36 would be approximately three millimeters. Normally, the location of the slots 34 and 36 is at the mid point of the distance between the front end 28 and the forward end 42 of the mounting pocket 30. The base plate 12 also includes a pair of holes 44 and 46 which may be used to fixate the device as by sutures.

The housing 20 is to be glued by glue layer 48 within the mounting pocket 30. The housing 20 is to closely conform to the pocket 30. The internal chamber 18 has an access opening 50. This access opening 50 is to be stretched so as to permit passage there through of the block 22 so as to position it in a snug fitting manner within the internal chamber 18.

This access opening 50 is to be covered by a canopy 52. The canopy 52 is to be integral with the housing 20. Basically, the shape of the canopy 52 is semi-circular. The outer tips 54 and 56 of the canopy 52 are to rest against the top surface 26 of the base plate 12. The canopy 52 defines an internal channel 58 which connects the ambient to the access opening 50.

The bottom surface 62 of the base plate 12 includes an enlarged recess 64 which is about 0.10 millimeters deep and much larger in size than said mounting pocket 30. The purpose of the recess 64 is to help form a bleb.

Figure 4:
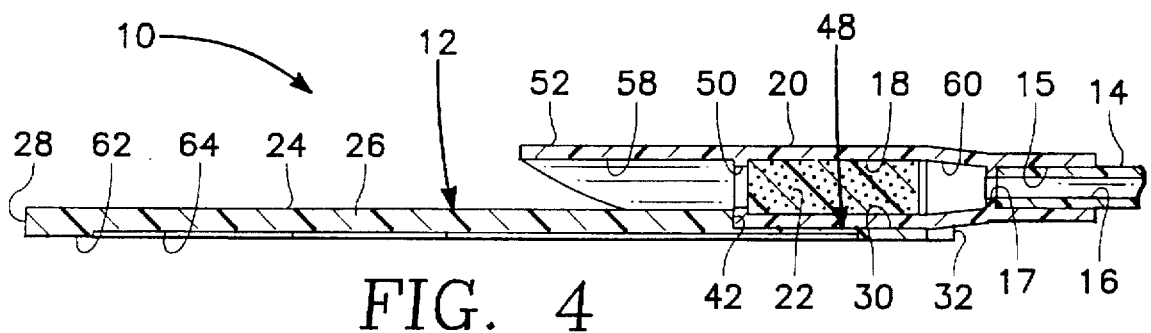
FIG. 4 is a longitudinal cross-sectional view of the glaucoma pressure regulator of the present invention taken along line 4—4 of FIG. 3.
Figure 5:
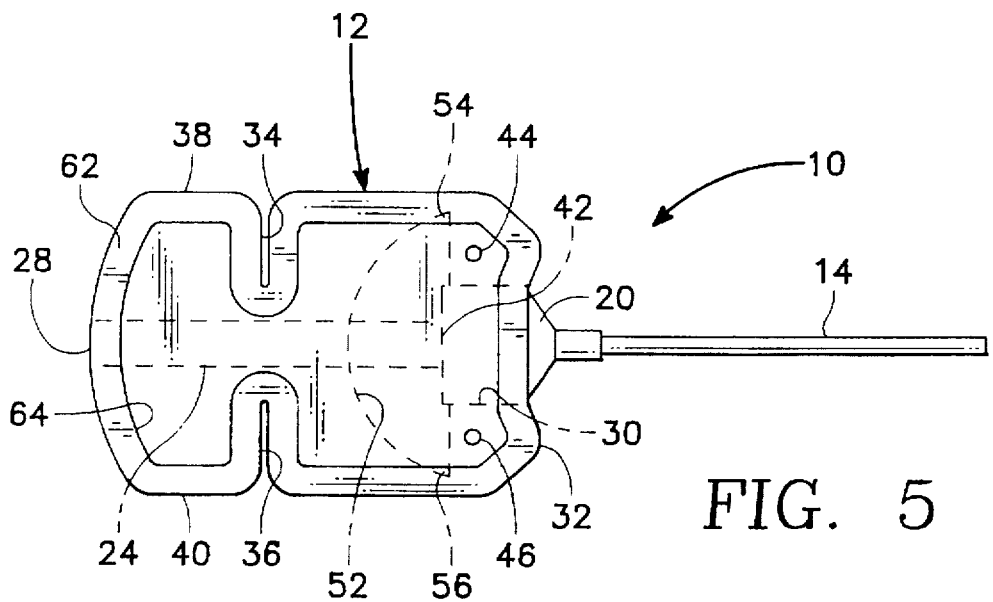
FIG. 5 is a bottom plan view of the glaucoma pressure regulator of the present invention.

When the base plate 12 is surgically installed underneath a flap (not shown) that is surgically performed within the eyeball (not shown), and the tube 14 is installed as previously mentioned within the anterior chamber, the aqueous humor from the anterior chamber is capable of flowing through the passage 16 to within collecting chamber 60 of the housing 20. From the collecting chamber 60, the fluid seeps through the porous block 22 and passes through access opening 50 into internal channel 58. From the internal channel 58 the aqueous humor is conducted onto the outer surface of the base plate 12 from where it is then discharged into the conjunctival space. For a pars plana application, the tube 14 will be formed at an angle (usually about ninety degrees) to the longitudinal direction of the pressure regulator 10 shown in FIG. 4 to more appropriately place the tube 14 in the pars plana portion of the eye.

What is claimed is:

1. A glaucoma pressure regulator adapted to be implanted within the conjunctiva of an eyeball, said regulator comprising:

a thin, flexible base plate having a front edge and a rear edge, side edges interconnecting said front edge and said rear edge, said base plate having a bottom surface and a top surface, said top surface including a first recessed area forming a mounting pocket;

a housing having an internal chamber, said housing being fixedly mounted within said mounting pocket, said housing having a front end and a rear end, said front end being open forming an access opening, said rear end being connected to a drainage tube; and a porous block mounted within said internal chamber, aqueous humor from said tube must flow through said porous block before exiting said housing at said front end.

2. The glaucoma pressure regulator as defined in claim 1 wherein:

said base plate being constructed of silicone rubber.

3. The glaucoma pressure regulator as defined in claim 1 wherein:

said base plate including a first side slot and second side slot, said first side slot connecting from one of said side edges and extending within said base plate, said second side slot extending from the other of said side edges and extending within said base plate, said side slots increasing the flexibility of said base plate.

4. The glaucoma pressure regulator as defined in claim 1 wherein:

said mounting pocket connecting with said rear edge, said mounting pocket being spaced from both said side edges.

5. The glaucoma pressure regulator as defined in claim 1 wherein:

a canopy attached to said front end of said housing, said canopy covering entirely said access opening.

6. The glaucoma pressure regulator as defined in claim 1 wherein:

said porous block comprising a molded, open cell, high density polyethylene polymer with a nominal porosity of eleven microns.

7. The glaucoma pressure regulator as defined in claim 1 wherein:

said bottom surface including a second recessed area, said second recessed area being substantially larger than said first recessed area, said second recessed area functioning as a bleb when mounted within the eyeball.

* * * * *